(12) United States Patent
Jezierski et al.

(10) Patent No.: US 9,468,455 B2
(45) Date of Patent: Oct. 18, 2016

(54) DRIVE SHAFT FOR A SURGICAL TOOL

(71) Applicant: Smith & Nephew, Inc., Memphis, TN (US)

(72) Inventors: Rafal Z. Jezierski, Middleton, MA (US); Peter M. Cesarini, Londonderry, NH (US)

(73) Assignee: Smith & Nephew, Inc., Memphis, TN (US)

( * ) Notice: Subject to any disclaimer, the term of this patent is extended or adjusted under 35 U.S.C. 154(b) by 45 days.

(21) Appl. No.: 14/592,202

(22) Filed: Jan. 8, 2015

(65) Prior Publication Data
US 2015/0119919 A1    Apr. 30, 2015

Related U.S. Application Data

(63) Continuation of application No. 12/235,045, filed on Sep. 22, 2008, now Pat. No. 8,945,165.

(51) Int. Cl.
*A61B 17/32* (2006.01)
*A61B 17/16* (2006.01)

(52) U.S. Cl.
CPC ... *A61B 17/320016* (2013.01); *A61B 17/1631* (2013.01); *A61B 17/32002* (2013.01); *Y10T 29/49826* (2015.01)

(58) Field of Classification Search
CPC ............ A61B 17/162; A61B 17/1631; A61B 17/1633; A61B 17/320016; A61B 17/32002; A61B 2017/00398; A61B 2017/00477
See application file for complete search history.

(56) References Cited

U.S. PATENT DOCUMENTS

| | | | |
|---|---|---|---|
| 1,269,971 A * | 6/1918 | Smith | 411/393 |
| 3,058,218 A | 10/1962 | Kieesattel et al. | |
| 3,721,154 A | 3/1973 | Leibinger et al. | |
| 5,133,729 A * | 7/1992 | Sjostrom | 606/180 |
| 5,188,531 A | 2/1993 | Von Sutfin | |
| 5,330,480 A * | 7/1994 | Meloul et al. | 606/80 |
| 6,575,280 B2 | 6/2003 | Ballew et al. | |
| 2001/0039428 A1 * | 11/2001 | Dinger et al. | 606/167 |
| 2002/0058958 A1 | 5/2002 | Walen | |
| 2002/0185353 A1 * | 12/2002 | Ballew et al. | 192/45.1 |
| 2006/0142656 A1 * | 6/2006 | Malackowski et al. | 600/424 |
| 2009/0012529 A1 * | 1/2009 | Blain et al. | 606/99 |
| 2010/0030263 A1 * | 2/2010 | Cheng et al. | 606/232 |
| 2010/0076477 A1 | 3/2010 | Jezierski et al. | |
| 2010/0249801 A1 | 9/2010 | Sengun et al. | |

FOREIGN PATENT DOCUMENTS

| | | |
|---|---|---|
| DE | 1214827 B | 4/1966 |
| DE | 202004017282 | 2/2005 |

(Continued)

OTHER PUBLICATIONS

Search Report from the State Intellectual Property Office of People's Republic of China for Chinese Patent Application No. 200980137249.4, dated Oct. 22, 2012.

(Continued)

*Primary Examiner* — Julie A Szpira

(57) ABSTRACT

The present disclosure relates to a drive shaft for a surgical handpiece including a first prong and a second prong, wherein the first prong and the second prong are asymmetric. A surgical handpiece and a method of coupling a surgical handpiece and a cutting tool are also disclosed.

8 Claims, 4 Drawing Sheets

(56) References Cited

FOREIGN PATENT DOCUMENTS

| EP | 0471533 A1 | 8/1991 |
|----|------------|--------|
| EP | 0866674 B1 | 1/2004 |
| WO | 8904238    | 5/1989 |

OTHER PUBLICATIONS

International Search Report and Written Opinion for PCT/US2009/054115 dated Dec. 17, 2009.

Fourth Office Action from the State Intellectual Property Office of People's Republic of China for Chinese Patent Application No. 200980137249.4, dated Aug. 15, 2014.

Decision of Rejection for Japanese Application No. 2011-527859, mailed May 7, 2014.

Patent Examination Report No. 1 for Australian Patent Application No. 20099293561, dated Sep. 28, 2014.

Notice for Reasons for Rejection, dated Jul. 14, 2015, 6 pages. (Citation 1 U.S. Pat. No. 3,721,154 has been previously cited.).

* cited by examiner

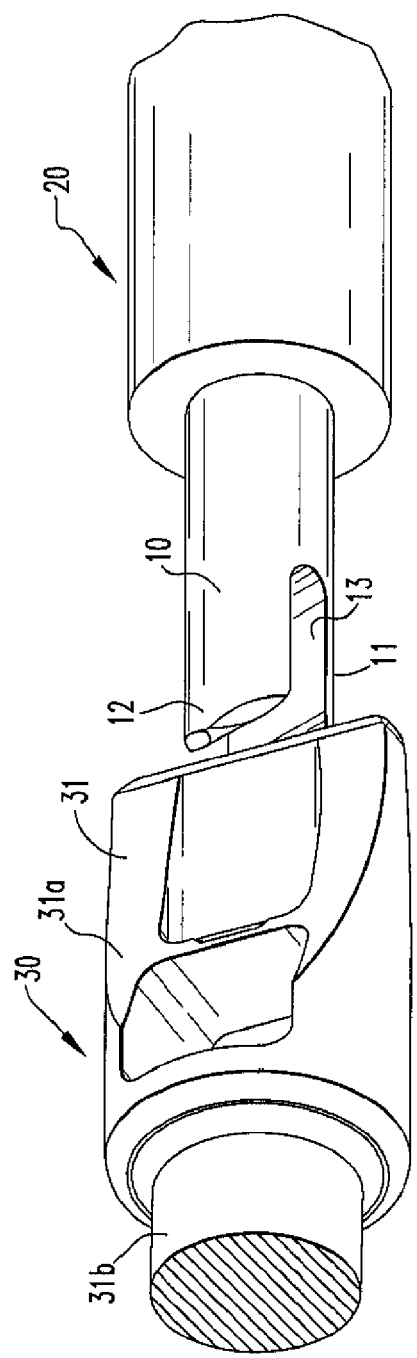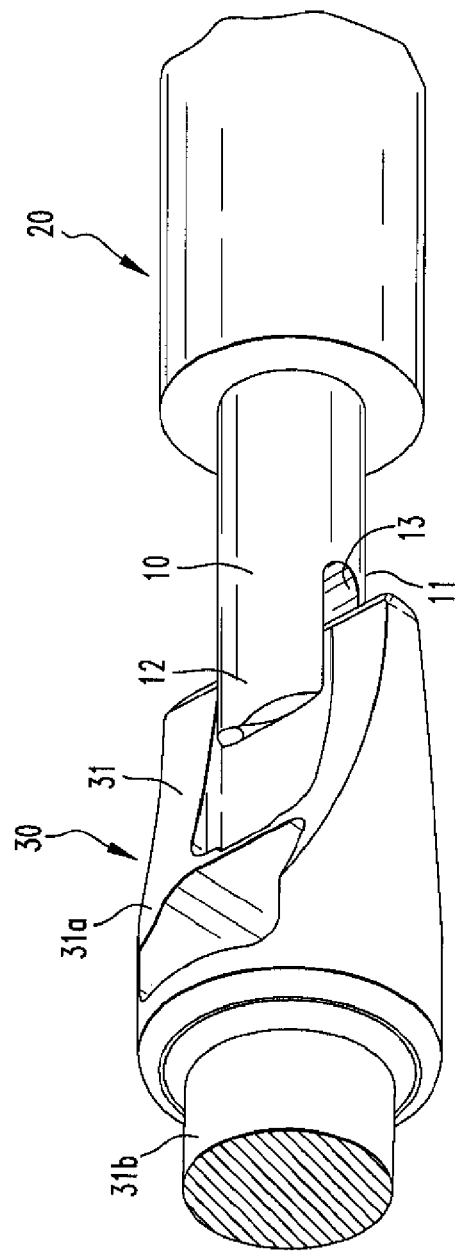

DRIVE SHAFT FOR A SURGICAL TOOL

CROSS REFERENCE TO RELATED APPLICATIONS

This application is a continuation application of co-pending U.S. patent application Ser. No. 12/235,045 filed Sep. 22, 2008 entitled DRIVE SHAFT FOR A SURGICAL TOOL.

TECHNICAL FIELD

The present disclosure relates to surgical handpieces, and more specifically to a drive shaft for a surgical handpiece.

BACKGROUND

Elongate surgical cutting tools have been used in performing closed surgery, such as endoscopic surgery, i.e., arthroscopic surgery. A drive tang on an inner member of the cutting tool is adapted to be driven via a drive shaft of a surgical handpiece that is coupled to the cutting tool. Currently, these drive shafts utilize a symmetrical drive fork design. The drive fork includes a fixed width slot, which is located along the axis of the drive shaft and centered around the same. The two prongs created by slotting the drive shaft are symmetrical and incorporate tapered and rounded ends. These ends facilitate engagement of the drive shaft with the drive tang such that the drive tang is inserted into the slot between the prongs and subsequently held by the prongs during operation of the handpiece. However, if the drive tang is not aligned with the slot, full engagement of the drive tang and the drive shaft fails to occur. In addition, due to this misalignment, damage may occur to the drive tang by the operator unknowingly attempting to force the drive tang into the handpiece.

Therefore, a drive shaft that allows for improved engagement between the drive tang and the handpiece is needed.

SUMMARY

In one aspect, the present disclosure relates to a drive shaft for a surgical handpiece including a first prong and a second prong, wherein the first prong and the second prong are asymmetric. In an embodiment, a slot is located between the first prong and the second prong. In another embodiment, the first prong is longer than the second prong. In yet another embodiment, both the first prong and the second prong include a tapered and rounded end. In a further embodiment, the end of the first prong is tapered and rounded at angles that are different from the angles of the tapered and rounded end of the second prong. In yet a further embodiment, the end of the first prong is tapered and rounded at angles that are the same as the angles of the tapered and rounded end of the second prong. In an embodiment, the end of the first prong is tapered at an angle of between about 45° and about 150° and rounded at a radius of between about 0.045 inches and about 0.250 inches. In another embodiment, the end of the second prong is tapered at an angle of between about 45° and about 150° and rounded at a radius of between about 0.045 inches and about 0.250 inches.

In another aspect, the present disclosure relates to a surgical handpiece including a drive shaft having a first prong and a second prong, wherein the first prong and the second prong are asymmetric.

In yet another aspect, the present disclosure relates to a method of coupling a surgical handpiece to a cutting tool. The method includes providing a surgical handpiece including a drive shaft having a first prong and a second prong, wherein the first prong and the second prong are asymmetric; providing a cutting tool comprising an inner member and an outer member; and coupling the handpiece to the cutting tool such that the drive shaft is coupled to a drive tang on the inner member of the cutting tool. In an embodiment, coupling of the drive shaft to the drive tang occurs such that the first prong causes rotation and subsequent insertion of the drive tang into a slot located between the first prong and the second prong.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 3A-3E show a method of coupling the drive shaft of FIGS. 1 and 2 to a cutting tool.

DETAILED DESCRIPTION

The disclosure of U.S. patent application Ser. No. 12/235,045 filed Sep. 22, 2008 entitled DRIVE SHAFT FOR A SURGICAL TOOL is hereby incorporated herein by reference in its entirety.

The following description of the preferred embodiment(s) is merely exemplary in nature and is in no way intended to limit the disclosure, its application, or uses.

Figure 1:
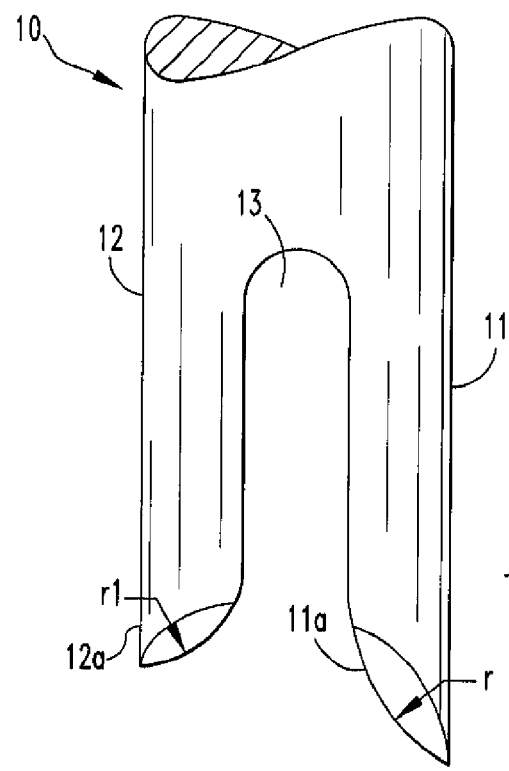
FIG. 1 shows a side view of the drive shaft of the present disclosure.
Figure 2:
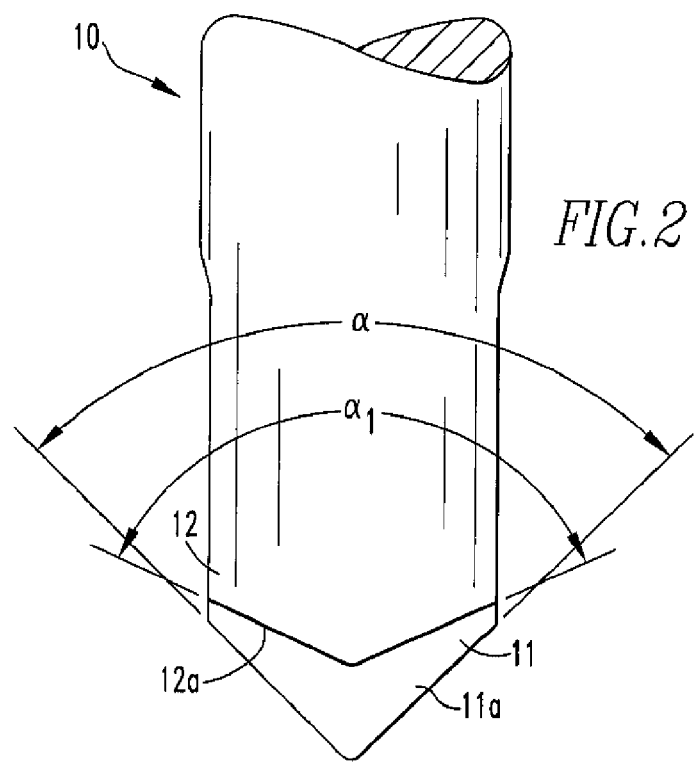
FIG. 2 shows a top view of the drive shaft of the present disclosure.

FIGS. 1 and 2 show the drive shaft 10 of the present disclosure. The shaft 10 includes a first prong 11, a second prong 12, and a slot 13 located between the first prong 11 and the second prong 12. The first prong 11 is longer than the second prong 12, thereby making the drive shaft 10 asymmetric. The purpose for the asymmetric drive shaft 10 will be further described below. Each prong 11, 12 has a tapered and rounded end 11a, 12a. As shown in FIGS. 1 and 2, the end 11a of the first prong 11 is tapered and rounded at an angle $\alpha$ and a radius r that is different from the angle $\alpha_1$ and radius $r_1$ of the tapered and rounded end 12a of the second prong 12. For instance, the end 11a of the first prong 11 is tapered and rounded at an angle $\alpha$ of about 90° and at a radius r of about 0.095 inches and the end 12a of the second prong 12 is tapered at an angle $\alpha_1$ of about 130° and a radius $r_1$ of about 0.050 inches. However, the end 11a of the first prong 11 may be tapered and rounded at an angle $\alpha$ and a radius r that is the same as the angle $\alpha_1$ and the radius $r_1$ of the tapered and rounded end 12a of the second end 12. For the purposes of this disclosure, the ends 11a, 12a of the prongs 11, 12 may be tapered at angles $\alpha$, $\alpha_1$ of between about 45° and about 150° and rounded at radii r, $r_1$ of between about 0.045 inches and about 0.250 inches.

Figure 3A:
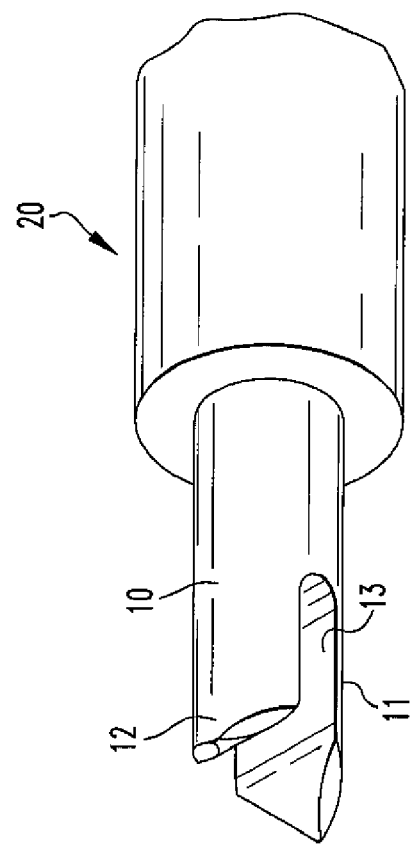
Figure 3A:
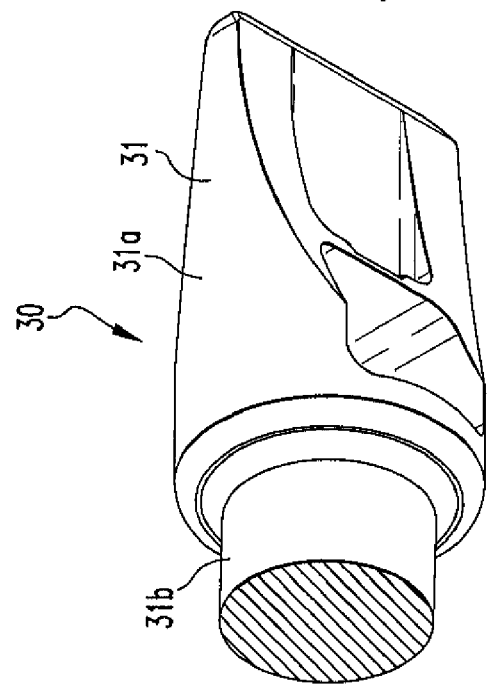
Figure 3B:
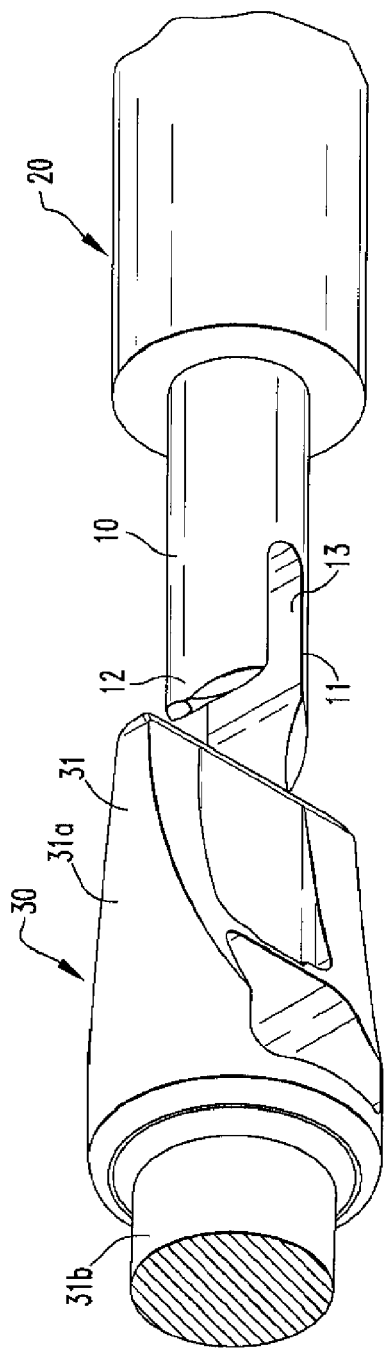
Figure 3C:
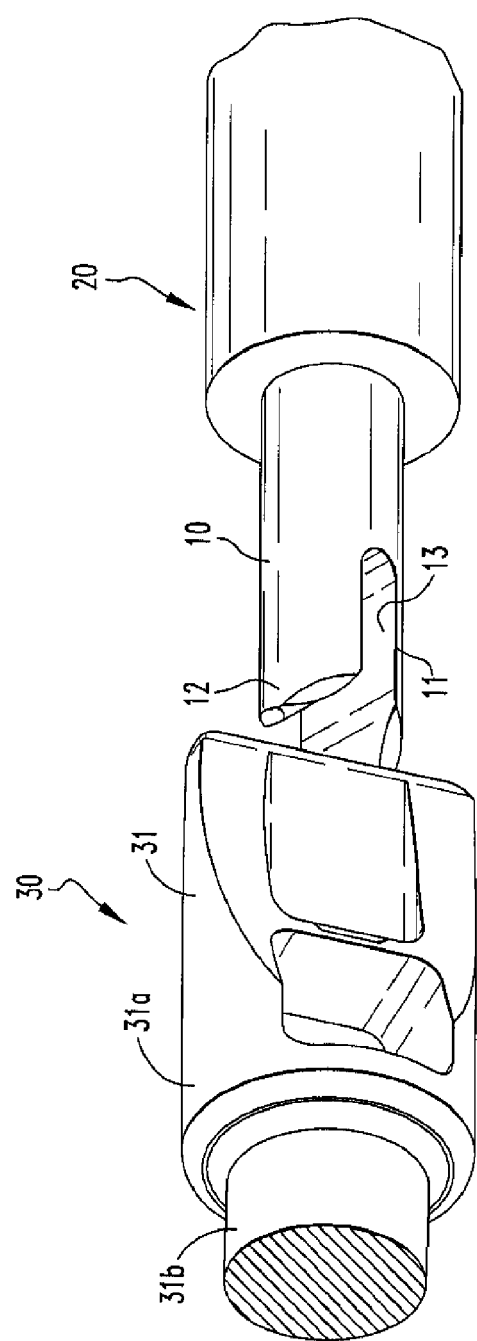

FIGS. 3A-3E show coupling of a surgical handpiece 20, including the drive shaft 10, to a cutting tool 30. For the purposes of this disclosure, only the inner member 31 of the cutting tool 30 is shown. However, in practice, the cutting tool 30 will include both an outer member and an inner member, as more fully explained in U.S. Pat. No. 5,871,493, which is incorporated herein by reference in its entirety. The inner member 31 includes a drive tang 31a coupled to a shaft 31b. The handpiece 20 is coupled to the inner member 31 such that the first prong 11 contacts the drive tang 31a, as shown in FIG. 3B, and causes rotation and subsequent insertion of the drive tang 31a into the slot 13, as shown in FIGS. 3C-3E, thereby allowing for full engagement of the drive tang 31a and the drive shaft 10.

As shown above, the drive shaft 10 of the present disclosure allows for full engagement between the drive tang 31a and the drive shaft 10 even when the drive tang 31a is not aligned with the slot 13 on the drive shaft 10. This improves user safety by reducing the possibility of a partially engaged cutting tool or the possibility of disengagement of a damaged cutting tool from the handpiece. In addition, the need for repeated insertion and removal of the cutting tool from the handpiece to ensure full engagement is also reduced.

The dive shaft 10 of the present disclosure is of a metal material. The prongs 11, 12 and the slot 13 of the drive shaft 10 are made via a machining process or any other process known to one of skill in the art. The drive shaft 10 is coupled to the handpiece 20 via a direct coupling with the motor of the drive shaft 10 or an indirect coupling with the motor via a component, such as a gearbox. The drive tang 31a of the inner member 30 is of a non-metal material and is made via an injection molding process or another process known to one of skill in the art. The shaft 31b, which is of a metal material, and the drive tang 31a may be coupled via a molding process or any other process known to one of skill in the art.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A surgical handpiece, comprising:
a drive shaft having a first prong and a second prong,
wherein the first prong and the second prong extend distally from the drive shaft,
wherein the first prong and the second prong define a slot therebetween,
wherein the first prong and the second prong each have a length, a width, and a thickness,
wherein the length of the first prong is longer than the length of the second prong,
wherein the first prong is symmetrically tapered along the width thereof at a first angle to a first point, thereby forming a pair of first symmetrical angled portions of the first prong that meet at the first point, each first symmetrical angled portion having a periphery,
wherein each first symmetrical angled portion of the first prong is rounded at a first radius along the periphery thereof, and
wherein each symmetrical angled portion of the first prong is operative to contact a drive tang, and to cause rotation of the drive tang, thereby allowing insertion of the drive tang into the slot between the first prong and the second prong.

2. The surgical handpiece of claim 1 wherein the second prong is symmetrically tapered along the width thereof at a second angle to a second point, thereby forming a pair of second symmetrical angled portions of the second prong that meet at the second point, each second symmetrical angled portion having a periphery, and wherein each second symmetrical angled portion of the second prong is rounded at a second radius along the periphery thereof.

3. The surgical handpiece of claim 2 wherein the first angle is different from the second angle, and the first radius is different from the second radius.

4. The surgical handpiece of claim 2 wherein the first angle is the same as the second angle, and the first radius is the same as the second radius.

5. The surgical handpiece of claim 2 wherein the first angle is between about 45° and about 150°, and the first radius is between about 0.045 inches and about 0.250 inches.

6. The surgical handpiece of claim 2 wherein the second angle is between about 45° and about 150°, and the second radius is between about 0.045 inches and about 0.250 inches.

7. A method of coupling a surgical handpiece to a cutting tool, comprising:
providing a surgical handpiece including a drive shaft, the drive shaft having a first prong and a second prong, the first prong and the second prong extending distally from the drive shaft, the first prong and the second prong defining a slot therebetween, wherein the first prong and the second prong each have a length, a width, and a thickness, the length of the first prong being longer than the length of the second prong, and wherein the first prong is symmetrically tapered along the width thereof at a first angle to a point, thereby forming a pair of symmetrical angled portions of the first prong that meet at the first point, each symmetrical angled portion having a periphery and being rounded at a first radius along the periphery thereof;
contacting one of the symmetrical angled portions of the first prong to a drive tang to cause rotation of the drive tang; and
inserting the drive tang into the slot between the first prong and the second prong.

8. The method of claim 7 wherein the first angle is between about 45° and about 150°, and the first radius is between about 0.045 inches and about 0.250 inches.

* * * * *